United States Patent [19]
Lerner et al.

[11] Patent Number: 5,959,172
[45] Date of Patent: Sep. 28, 1999

[54] GENDER-SPECIFIC FADING DOWN TURKEY BREED

[75] Inventors: Steven Lerner, Lewisburg, W. Va.; V. Hugh C. Arnold, Chester, United Kingdom; D. S. Carol Harvey, Cornwall, United Kingdom; John C. Francis, Chester, United Kingdom

[73] Assignee: Merck & Co., Inc., Rahway, N.J.

[21] Appl. No.: 08/757,497

[22] Filed: Nov. 27, 1996

Related U.S. Application Data

[60] Provisional application No. 60/007,795, Nov. 30, 1995.

[51] Int. Cl.$^6$ .............................. C12N 5/00; C12N 15/00
[52] U.S. Cl. ................. 800/2; 800/DIG. 3; 800/DIG. 4; 435/172.1
[58] Field of Search .................................. 800/2, DIG. 3, 800/DIG. 4; 536/23.1; 435/172.1

[56] References Cited

PUBLICATIONS

Asmundson, "Sex Linkage in the Turkey", J. Heredity, 41: 205–207 (1950).

Buss, et al., "The Influence of Sex Genes Affecting Feather Colour on the 24–week Body Weight of Turkeys", Poultry Sci., 39: 1238–1239, 1960).

Hann, "Sex Linkage in Poultry Breeding", Bulletin No. 38, Ministry of Agriculture, Fisheries and Food, H.M.S.O., 1966.

Nestor, et al., "Genetics of Growth and Reproduction in the Turkey, 6. Influenxe of Plumage Color Pattern Genes on Mortality, Body Weight . . . ", Poultry Sci., 58: 1137–1142.

Campo, et al., "Genetics of the Birchen and Blue Plumage Patterns in Leonesa Chickens", Poultry Science, vol. 72, pp. 1218–1223, 1993.

Campo, et al., "Use of Sex–Linked Barring (B) Gene for Chick Sexing on an Euroclanotic Columbian Background", Poultry Science, vol. 70, No. 7, pp. 1469–1473, 1991.

*Primary Examiner*—Deborah Crouch
*Attorney, Agent, or Firm*—Michael D. Yablonsky; Jack L. Tribble

[57] ABSTRACT

The present invention relates to a method of rapidly determining the gender of fowl. The present invention further relates to a new breed of turkey.

2 Claims, No Drawings

GENDER-SPECIFIC FADING DOWN TURKEY BREED

This application claims benefit of provisional application No. 60/007,795 filed Nov. 30, 1995.

CROSS-REFERENCE TO RELATED APPLICATIONS

Not applicable.

STATEMENT REGARDING FEDERALLY-SPONSORED R&D

Not applicable.

REFERENCE TO MICROFICHE APPENDIX

Not applicable.

FIELD OF THE INVENTION

The present invention relates to a method of rapidly determining the gender of fowl. The present invention further relates to a new breed of turkey. The invention further realtes to DNA molecules which regulate the expression of color in the down in the new breed of turkey.

BACKGROUND OF THE INVENTION

The present invention relates to a method of rapidly determining the gender of fowl. The present invention relates to a new breed of turkey, designated as Gender-specific Fading Down (GFD).

The commercial production of breeding turkeys requires the separation of newly-hatched poults by gender; that is, male poults from female poults. Prior to the early 1960's, commercial turkeys were mostly color-feathered and the breeding methods practiced then provided a system of separating poults based on the color of their down at hatch; i.e. the down of female poults was one color, while that of the male poults was another color. This method was referred to as color sexing'. However, during the early 1960's, commercial breeders and processors, who had difficultly removing unsightly dark pin feathers from color-feathered turkeys, demanded the selection and propagation of white-feathered commercial birds. These birds contain a "White gene" that prevents the expression of color in the down of the poult and in the feathers of the adult. This change made color sexing impossible.

Currently, the gender of a poult is determined by visual or mechanical examination of its genital region (commonly referred as its cloaca or vent) shortly after hatch. The examination is typically accomplished by a specially-trained human being with or without the aid of a mechanical sensor. While commercially acceptable, several problems arise from this method of determining gender. First, it is not absolutely accurate: male poults can be misidentified as female poults. Secondly, the process of examination requires extensive physical manipulation of the poult, including modest pressure on the bowel to express feces from the lower digestive tract, spreading of the legs to view the genital region, and finger-tip manipulation of the genital region itself to make identifying characteristics visible. This procedure is stressful to the poults at best and causes physical damage at worst. Damaged poults fail to thrive and will result in an economic loss. Third, the nature of this procedure promotes the spread of disease through flocks. An infectious agent from a single infected poult can be transferred to the human examiner and subsequently transferred to previously uninfected birds. Diseased poults will fail to thrive and will result in an economic loss. Fourth, this method of examination is time-consuming.

It would be advantageous to determine the gender of turkeys without having to examine the genital region in the aforementioned manner.

The present invention is a new breed of turkey, designated as Gender-specific Fading Down (GFD). The GFD breed of turkey contains a genetic mutation which suppresses the genetic effect of the White gene in the poult, but not in the adult. Newly hatched poults of GFD parentage have gender-specific colored down. Male poults have black down while female poults have brown down. This color difference facilitates rapid, accurate separation of poults by gender. As the turkeys grow, the suppressive action of the genetic mutation fades, and the colored down is replaced by white plumage. At commercially relevant ages, the turkeys are completely white. The fading characteristic of this mutation is paramount in the production of desirable white turkeys.

SUMMARY OF THE INVENTION

The present invention relates to a method of rapidly determining the gender of fowl. The present invention further relates to a new breed of turkey.

BRIEF DESCRIPTION OF THE DRAWINGS

Not applicable.

DETAILED DESCRIPTION OF THE INVENTION

The present invention relates to a method of rapidly determining the gender of fowl. The present invention further relates to a new breed of turkey.

Currently, the gender of a poult is determined by visual or mechanical examination of its genital region (commonly referred as its cloaca or vent) shortly after hatch. The examination is typically accomplished by a specially-trained human being with or without the aid of a mechanical sensor. While commercially acceptable, several problems arise from this method of determining gender. First, it is not absolutely accurate: male poults can be misidentified as female poults. Secondly, the process of examination requires extensive physical manipulation of the poult, including modest pressure on the bowel to express feces from the lower digestive tract, spreading of the legs to view the genital region, and finger-tip manipulation of the genital region itself to make identifying characteristics visible. This procedure is stressful to the poults at best and causes physical damage at worst. Damaged poults fail to thrive and will result in an economic loss. Third, the nature of this procedure promotes the spread of disease through flocks. An infectious agent from a single infected poult can be transferred to the human examiner and subsequently transferred to previously uninfected birds. Diseased poults will fail to thrive and will result in an economic loss. Fourth, this method of examination is time-consuming.

One object of the present invention is to provide a method of determining the gender of a poult without examination of its genital region. Another object of the invention is to provide a more rapid method of separating male and female poults. Still another object of the present invention is to provide a new breed of turkey that produces poults that can be separated without examination of the genital region. A further object of the invention is to provide a less expensive method of separating male and female poults.

The new breed of turkey of the present invention is designated as Gender-specific Fading Down (GFD). The GFD breed of turkey contains a unique genetic mutation which suppresses the masking or epistatic effect of the recessive White gene and permits the expression of hidden or cryptomeric color genes. Newly hatch poults of GFD parentage have colored down. The colored down is progressively replaced by white plumage such that by commercially-relevant ages the turkey is completely white. The color of the down is linked to the gender of the poult: male poults have different colored down than that of female poults. The difference in color enables inexperienced personnel to rapidly separate male and female poults and completely eliminates the need for examination of the genital region.

The nature of the poultry industry requires two breeds of turkeys to produce a profitable commercial product: a so-called male-line and a female-line. Production, development, and maintenance of these separate breeds is the business of the Primary Turkey Breeder, of which BUT is one. A male-line is bred for its physical characteristics that result in rapid development of muscle and hence provide large quantities of meat. Male characteristics are highly heritable and will be passed on to subsequent generations. A female-line is bred for prolificacy; i.e. lays larger numbers of fertile, hatchable eggs. Primary breeders provide to the market male-line toms and female-line hens, which when bred produce large numbers of eggs that hatch to yield rapidly growing poults.

To add a rapid method of gender determination, producers of commercial turkeys would acquire toms from a GFD breed. At maturity, these toms would be crossed with hens of a commercial white-feathered female-line to produce large numbers of gender-specific colored poults that grew rapidly with white plumage.

The following examples are provided for the purpose of illustrating the present invention without, however, limiting the same thereto.

EXAMPLE 1
Production of the Rodda Breeding Stock

In 1971 on the Rodda Farm a double-yolked egg hatched Siamese twins. These poults had black colored down that was replaced by white feathers as the birds grew. The male turkey was crossed with white-feathered hens. Some of the resulting offspring had black colored down which faded to white plumage. Poults that possessed this trait (designated "Fading Down" or FD) were selected out of the population, raised to maturity, and crossed with white-feather birds to produce the next generation of poults. Expression of color in the down was not related to the gender of the poult. Over the next ten years, extensive cross breeding and selection for intensity of color in the down resulted in the generation of a population of breeding stock that was pure or homozygous for an intense black colored down which faded in the adult. This FD breeding stock, via selection goals, was made free of two undesirable genetic factors: a Red gene, which is associated with undesirable commercial performance, and Diluter genes, which suppress the expression of color in the down.

It is well established in poultry that certain feather colors are genetically linked to the genes that determine gender (See Example 4). One such color is Auburn (or Brown). In 1982, Dr. Ed Buss provided eggs from an Auburn-feathered breed of turkeys. From this initial seed, a population of breeding stock was produced which were selected to be pure for the Auburn color. The Auburn color was introduced into the FD breeding stock to enable the linking of colored down with gender. Development of the breeding stock continued through selection for depth of color and fading ability. In 1985, Rodda put their FD breeding stock on the market.

EXAMPLE 2
Production of the BUT FD Breeding Stock

Contemporary to the introduction of the Rodda breed on the market, BUT began an extensive testing program designed to identify poults that possess a "Fading" gene. From a starting population of three million poults hatched at BUT, approximately one hundred naturally-occurring colored poults were identified and followed to adulthood. Of those examined, only one female poult was found that possessed a dark-colored down, but pure white plumage as an adult. This hen was inseminated weekly and was allowed to produce eggs for a period of two years. Eggs were collected daily, marked for purposes of identification to the hen, set for incubation, and hatch forthnightly. All of the progeny from this hen that hatched with colored down, but subsequently faded to white, were kept and used as BUT FD breeding stock. To improve the commercial performance of this stock, it was crossed and back-crossed with our largest, most rapidly-growing breed, the BUT 78.

EXAMPLE 3
Development of the GFD Breeding Stock

In 1987, BUT began work with the Rodda FD breeding stock. The Rodda turkey was small and poorly fleshed, and hence not acceptable as a commercial breed. To correct that problem, the Rodda bird was crossed with BUT 78 and BUT 42 breeding stock. Repeated back-crosses were performed with selection of the FD trait and commercially-desirable carcass characteristics; these breeding stocks were designated as the BUT 78 Auburn and BUT 42 Auburn. Poults of this parentage were hatched with gender-specific colored down that faded to white plumage. The introduction of the BUT genetic background onto the Rodda turkey resulted in the gradual, but continuous loss of intensity of color in the down of poults. In addition, an undesirable light brown color was expressed by the poults of this parentage.

In 1989, it was decided to cross the BUT FD breeding stock into the BUT Auburn breeds and to test for gender-specific expression of color, intensity of color, and fading. Results showed that the two genes, the Rodda FD gene and the BUT FD gene, work in concert to enhance the color of the down of the poults. The color of the down was completely gender-specific and faded to white plumage. This breeding stock continues to be developed for commercial use and is designated as Gender-specific Fading Down. Blastodermal cells from the Gender-Specific Fading Down Turkey Breed, were deposited in the European Collection of Cell Cultures, Centre of Applied Microbiology & Research, Salisbury, Wiltshire, SP4 0JG, United Kingdom, on Jul. 03, 1998 under the terms of the Budapest Treaty and were designated as ECACC Accession No. 98070316. A license may be required to make, use, sell or offer to sell the turkeys of the Gender-Specific Fading Down Breed. No such license is granted herein.

EXAMPLE 4
Use of the GFD Breed

The nature of the poultry industry requires two breeds of turkeys to produce a profitable commercial product: a so-called male-line and a female-line. Production, development, and maintenance of these separate breeds is the business of the Primary Turkey Breeder, of which BUT is one. A male-line is bred for its physical characteristics that result in rapid development of muscle and hence provide large quantities of meat. Male characteristics are highly heritable and will be passed on to subsequent generations. A female-line is bred for prolificacy; i.e. lays larger numbers of fertile, hatchable eggs. Primary breeders provide to the market male-line toms and female-line hens, which when bred produce large numbers of eggs that hatch to yield rapidly growing poults.

To add a rapid method of gender determination, producers of commercial turkeys would acquire toms from a GFD breed. At maturity, these toms would be crossed with hens of a commercial white-feathered female-line to produce large numbers of gender-specific colored poults that grew rapidly with white plumage.

EXAMPLE 5

The genetic basis for gender-specific colored down in offspring of GFD sires. The genetic basis for gender-specific colored down is illustrated as follows. Auburn is a genetic recessive, gender-linked condition, commonly denoted by e. Please note that in avian species, males are homogametic while in mammals females are homogametic. Auburn feathered toms are homozygous for the Auburn allele, ee, while auburn females are hemizygous, e– (where the "–" designates the absence of a functional allele). The dominant condition is referred to as non-auburn and is denote, E. Non-auburn toms can be EE or Ee, while non-auburn hens must be E–. GFD toms are genetically auburn, but are phenotypically white because of the duel action of the two Fading genes. Commercial white-feathered hens are genetically non-auburn. A cross between GFD toms and commercial hens would yield male poults with black down (Ee) and female poults with auburn down (e–). The interactive, suppressive effects of the Fading Down genes on the White gene would be lost as the birds mature and the poults of this cross would be uniformly white at commercially-relevant ages.

EXAMPLE 6
Identification of the Fading Down genes

The GFD breed and the BUT 78 breed are congenic for the Fading Down genes and auburn color genes. That is they are genetically identical except for those three genes and any passenger genes that have not been removed from the population by repeated back-crossing. It is likely that there is less than 1% genetic polymorphism between these two breeds. By using various combinations of the commercially-available simple-sequence repeat (SSR) primers combined with polymerase chain reaction (PCR) techniques, polymorphic regions of DNA can be identified. Once identified and proven to be associated with the presence of any of the aforementioned genes, the SSR-marked polymorphic regions can be isolated and the genetic sequence of the gene can be determined using DNA sequencing techniques.

EXAMPLE 7
Molecular Cloning of Gender-specific Fading Down Genes

A partial-length cDNA clone both Gender-specific Fading Down genes are identified using a [32P]-labelled synthetic oligonucleotide probe. The initial clone is retrieved by DNA amplification using the PCR with synthetic oligonucleotide primers. The resulting amplification products are ligted into plasmid vectors such as pCR-II (Invitrogen), transformed into competent *Escherichia coli* (*E. coli*) cells, colony-purified and propagated by growth of the resulting transformed cells in liquid culture. The plasmid DNA's are purified from the cells and the nucleotide sequence of the clones are determined. The complete cDNA sequnece of the Gender-specific Fading Down genes and corresponding amino acid sequences are determined.

What is claimed:

1. A Gender-specific Fading Down (GFD) turkey, ECACC Accession No. 98070316.

2. A color-based method of determining the gender of turkey poults comprising:
   a) mating a GFD male turkey (ee) ECACC Accession No. 98070316 with an (E–) hen; and
   b) identifying auburn (e–) poults as female and black (Ee) poults as male.

* * * * *